(12) United States Patent
Toth et al.

(10) Patent No.: US 6,462,183 B1
(45) Date of Patent: Oct. 8, 2002

(54) PROTECTED AMINOSUGARS

(75) Inventors: Istvan Toth, Sherwood (AU); Gyula Dekany, Middlesex; Barry Kellam, Kent, both of (GB)

(73) Assignee: Alchemia Pty Ltd, Sherwood (AU)

( * ) Notice: Subject to any disclaimer, the term of this patent is extended or adjusted under 35 U.S.C. 154(b) by 0 days.

(21) Appl. No.: 09/380,194

(22) PCT Filed: Feb. 27, 1998

(86) PCT No.: PCT/AU98/00131

§ 371 (c)(1),
(2), (4) Date: Aug. 26, 1999

(87) PCT Pub. No.: WO98/38197

PCT Pub. Date: Sep. 3, 1998

(30) Foreign Application Priority Data

Feb. 28, 1997 (AU) .............................................. PO-5367

(51) Int. Cl.$^7$ ......................... C07H 15/20; C07H 15/22
(52) U.S. Cl. ...................... 536/17.2; 536/18.5; 536/124
(58) Field of Search ............................... 536/17.2, 18.5, 536/124

(56) References Cited

U.S. PATENT DOCUMENTS 4,062,950 A    12/1977    Frommer et al. ............ 424/181

FOREIGN PATENT DOCUMENTS

| WO | WO97/45421 | 12/1997 |
| WO | WO 98/08799 | 3/1998 |

OTHER PUBLICATIONS

Garcia Martin et al. "Glycosides of 1–amino–1–deoxy–D–fructose", Carbohydrate Res., vol. 199: 139–151, 1990.*

Ding et al. "Synthesis and Biological Activity of Oligosaccharide Libraries", Glycoimmunology, Plenum Press, pp. 261–269, 1995.*

Kahne et al. "Parallel Synthesis and Screening of a Solid Phase Carbohydrate Library", Science, vol. 274: 1520–1522, Nov. 1996.*

Sofia, Michael. "Chemical Strategies for Introducing Carbohydrate Molecular Diversity into the Drug Delivery Process", Retrieved from the Internet <URL: http://www-.netsci.org/Science/Combichem/feature12.htm [retrieved on Jul. 13, 1998].*

Protecting Groups in Organic Synthesis, ed. by Greene & Wuts, John Wiley & Sons, pp. 591–592, 1999.*

Kellam et al. "Solid phase strategies: Application of 2–acetyl–4–nitroindane–1, 3–dione as a selective protecting group for primary amines", Tetrahedron, vol. 54: 6817–6832, 1998.*

Bycroft et al., "A Novel Lysine–protecting Procedure for Continuous Flow Solid Phase Synthesis of Branched Peptides", *J. Chem. Soc., Chem. Commun.*, 778–779, 1993.

Chan et al., "Novel Protecting Group for Fmoc–tBu Solid–Phase Synthesis of Side–Chair Carboxy–Modified Peptides", *J. Chem.soc., Chem.commun.* (9), 153–154, 1993.

Nash et al., "Dde–A Selective Primary Amine Protecting Group: A Facile Solid Phase Synthetic Approach to Polyamine Conjugates," *Tetrahedron Letters*, 37(15):2625–2628, 1996.

International Search Report for parent application, PCT/AU98/00131.

Akhrem et al., "Reaction of some aromatic oxides of nitriles with dimedone," *Khim. Geterotsikl.* Soedin, 7:901–904, cited in CAPLUS as 1974:505372.

International Search Report from Hungarian Patent Office for Patent Application No. P0000819, dated Dec. 20, 2000, mailed to client Jan. 31, 2001, received by client Mar. 21, 2001.

Wipfler et al., "The Reactivity of the C=N–Double Bond System, XV[1] The reaction of Anilinomethylene–Barbituric Acids with Methylenactive Nitriles"; Z. Naturforsch, 33b:1016–1019, 1978, *with Translation*.

Supplemental Partial European Search Report for Patent Application No. EP 98 94 6145.4, dated Jan. 23, 2002.

* cited by examiner

*Primary Examiner*—James O. Wilson
*Assistant Examiner*—Lehigh C. Maier
(74) *Attorney, Agent, or Firm*—Williams, Morgan & Amerson

(57) ABSTRACT

The invention provides amine-protecting groups for use in solution phase or solid-phase oligosaccharide synthesis, in which a 2-substituted 1,3-dioxo compound is used to protect one or more primary amine groups of an aminosugar or gylycosylamine. The invention provides reagents, reagent kits, and methods for solution phase, solid-phase oligosaccharide synthesis.

17 Claims, No Drawings

PROTECTED AMINOSUGARS

The present application is a nationalization of International Patent Application PCT/AU98/00131, filed Feb. 27, 1998, which claims priority to Australian Patent Application PO 5367, filed Feb. 28, 1997.

This invention relates to methods for synthesis of oligosaccharides, especially those oligosaccharides which comprise amino sugar residues. In particular the invention relates to methods for solution phase, solid phase or combinatorial synthesis of oligosaccharides.

BACKGROUND OF THE INVENTION

Aminosugars are important constituents of various glycoconjugates (Schmidt and Kinzy, 1994). Examples include peptidoglycans, mucopolysaccharides, glycopeptides and proteins, oligosaccharides of human milk, and blood group determinants. They are often also encountered in bacterial and tumour-associated carbohydrate antigens, predominantly in the N-acetylated form or N-acylated with an aspartic acid residue (Toyokuni and Singhal, 1995). It is therefore evident that these biological glycoconjugates are of immense interest to the medicinal chemist, and therefore that there is a great need in the art to be able to synthesise these compounds in a facile and cost-effective manner.

Oligosaccharide synthesis using aminosugars requires the presence of a suitable amino protecting group. A number of protecting groups have been proposed, but so far all of the agents which are available suffer from serious disadvantages. For example, glycosylation with donors derived from 2-N-acetyl protected aminosugars proceeds via neighbouring group participation; however, formation of the relatively stable oxazoline intermediate dramatically reduces the overall speed and yield of the reaction (Zurabyan et al, 1994). Therefore, various 2-deoxy-2-aminosugar donors, displaying the neighbouring group activity described, but lacking the ability to form stable oxazolines, have been developed; the most widely used of these are the phthalimido protected monomers (Sasaki et al, 1978). The phthalimide group participates strongly during glycoside formation and gives excellent stereocontrol of the 1,2-trans-glycoside product (Lemieux et al, 1982), furthermore the aminosugar donors do not form stable orthoamides (Lemieux et al, 1982) and cannot form oxazolines. The major disadvantage of using the phthalimide group lies in the vigorous conditions required for its removal, namely heating with methanolic hydrazine, which often results in partial product decomposition. Strongly basic conditions are also required for the removal of the N-sulfonyl (Griffith and Danishefsky, 1990) and N-haloacetyl protecting groups (Shapiro et al, 1967), resulting in similar problems.

The allyloxycarbonyl (Alloc) protected amino sugar donors display a similar activity to their phthalimide counterparts when employed under Lewis acid-catalysed conditions. However, the Alloc group has the advantage that it can be removed under extremely mild conditions, using tetrakis (triphenylphosphine)palladium in the presence of a mild base (Hayakawa et al, 1986). The major disadvantage associated with the Alloc group lies in its ability to form a stable oxazolidinone intermediate, which in the presence of unreactive acceptors tends to remain as the major product, and reduces the speed and yield of the reaction (Boullanger et al, 1987). 2,2,2-Trichloroethyl-protected aminosugars contain a strongly participating group that, unlike phthalimide, does not deactivate adjacent hydroxyl groups which may subsequently be required as glycosyl acceptors. They can be removed under relatively mild and selective conditions, using zinc and acetic acid, and do not form oxazoline intermediates during glycosylation. However, this protecting group has the disadvantage that benzyl groups cannot be introduced without premature loss of the protecting group as well (Imoto et al, 1987).

Tetrachlorophthaloyl-protected aminosugar donors have been demonstrated to afford high yields of 1,2-trans-glycosides (Castro-Palomino and Schmidt, 1995), even in the presence of poorly reactive acceptors. Once more, however, the $NaBH_4$-mediated deprotection is the limiting factor for this particular protecting group.

The azide group has received much attention in aminosugar chemistry, since it serves as a masked, non-participating amino functionality, thereby allowing the synthesis of 1,2-cis-linked 2-amino-2-deoxy glycosides (Palsen, 1982). However the preparation of 2-azido-2-deoxy sugars is protracted, costly, and often dangerous, using either azidonitration (Lemieux and Ratcliffe, 1979), diazo-transfer reactions (Buskas et al, 1994), azidochlorination (Bovin et al, 1986), nitrosation of N-benzyl derivatives (Dasgupta and Garegg, 1989) or reactions of 1,6-anhydrosugars (Tailler et al, 1991 and Paulsen and Stenzel, 1978).

Other non-participating protecting groups that have been reported are 2,4-dinitrophenyl (Kaifu and Osawa, 1977) and p-methoxybenzylimino (Mootoo and Fraser-Reid, 1989), both of which are complicated to introduce and require harsh deprotection conditions which result in loss of product.

A hydrazine-labile primary amino-protecting group, N-1-(4,4-dimethyl-2,6-dioxocyclohexylidene)ethyl (Dde), has been reported for protection of lysine side chains during SPPS (Bycroft et al, 1993). This group was modified for use as a carboxy-protecting group in SPPS when the 2-(3-methylbutyryl)dimedone analogue of 2-acetyldimedone was condensed with 4-aminobenzylalcohol to afford 4-{N-[1-(4,4-dimethyl-2,6-dioxocyclo-hexylidene)-3-methylbutyl]-amino}benzyl ester (ODmab) (Chan et al, 1995). These two protecting groups were reported to be stable to the Fmoc deprotecting conditions widely used in solid phase peptide synthesis (SPPS), ie 20% piperidine in dimethylformamide (DMF).

Dde has been widely used in the field of SPPS as an orthogonal amino protecting group to the well established Fmoc/t-Boc methodology (Fields and Noble, 1990). Until now its use has remained within this area, and therefore its use as a protecting group in the field of carbohydrate chemistry is novel. In particular, the use of Dde or ODMab in oligosaccharide synthesis has not been suggested.

We have now surprisingly found that Dde can be used as a non-participating amino sugar protecting group, which can be introduced and removed in a facile and cost-effective manner. We have shown that the vinylogous amide protection afforded by the Dde type group is achieved by simply refluxing the unprotected amino sugar with the precursor, eg. 2-acetyldimedone in the case of Dde, in anhydrous ethanol. Using a Dde-protected aminosugar, we have performed a variety of chemical modifications upon the protected molecule in order to demonstrate the stability of this vinylogous amide type protection towards commonly encountered reactions involved in carbohydrate modification.

SUMMARY OF THE INVENTION

In one aspect, the invention provides a compound useful as a reagent for solution and/or solid phase synthesis of sugar-containing compounds, comprising a sugar carrying one or more primary amine groups protected with a 2-substituted-1,3-dioxo compound of General Formula I or General Formula II:

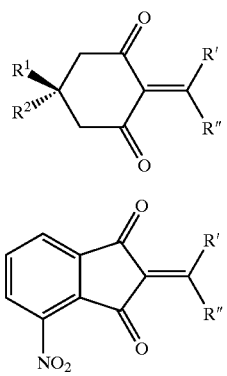

in which
R$^1$ and R$^2$ may be the same or different, and is each hydrogen or C$_{1-4}$ alkyl,
R' is an amino sugar, a glycosylamine, or an oligosaccharide comprising at least one aminosugar or one glycosylamine unit, in which the sugar is coupled via an amino group,
and R" is alkyl, substituted alkyl, aryl, substituted aryl, cycloalkyl or substituted cycloalkyl.

Any sugar or oligosaccharide bearing an amino group may be used.

In a preferred embodiment, the invention provides a reagent for solution phase synthesis of sugar-containing compounds, comprising a cyclic 2-substituted-1,3-dioxo compound of General Formula I or II as defined above, in which R' is as defined above.

The compounds of the invention are suitable for use in methods of solid-phase oligosaccharide synthesis, in which sugar units are covalently linked to a resin. Any suitable linker compound may be used. For example, the covalent linkage to the resin may suitably be provided by a —CONH—, —O—, —S—, —COO—, —CH═N—, —NHCONH—, —NHCSNH, or —NHNH— grouping, eg. Spacer— CONH-resin, Spacer-O-resin, Spacer-S-resin, Spacer-CO$_2$-resin, Spacer-CH═N-resin, Spacer-NHCONH-resin, Spacer-NHCSNH-resin, Spacer NHNH-resin. Other possible covalent linking groups will be known to those skilled in the art. It is contemplated that linkers and methods described in our International Patent Application No. PCT/AU97/00544 filed on Aug. 26, 1997, are suitable for use with the compounds of this invention. The entire disclosure of PCT/AU97/00544 is incorporated herein by this cross-reference. These linker systems enable solid phase synthesis of oligosaccharides under mild conditions analogous to those used for SPPS.

The resin may be any resin which swells in water and/or in an organic solvent, and which comprises one of the following substituents: halogen, hydroxy, carboxyl, SH, NH$_2$, formyl, SO$_2$NH$_2$, or NHNH$_2$, for example methylbenzhydrylamine (MBHA) resin, amino or carboxy tentagel resins, paraaminomethylbenzyl (PAM) resin, or 4-sulphamylbenzyl AM resin. Other suitable resins will be known to those skilled in the art.

Thus in a second aspect the invention provides a linker-saccharide complex, comprising a linker group and a saccharide compound comprising a protecting group of general formula I or II as defined above, in which the group R' is as defined above.

In a third aspect the invention provides a resin-linker-saccharide support for solid-phase oligosaccharide synthesis, comprising a linker group, a resin, and a starting saccharide compound comprising a protecting group of General Formula I or General Formula II as defined above, in which the group R' is as defined above.

Any suitable linker may be used. Again, it is contemplated that linkers and methods described in PCT/AU97/00544 may be used.

In a fourth aspect the invention provides a method of solid-phase synthesis of oligosaccharides, comprising the step of sequentially linking mono- or oligosaccharide groups, one or more of which is protected as described above, to a resin-linker-saccharide support as described above.

In a fifth aspect the invention provides a method of solution phase synthesis of oligosaccharides, comprising the step of sequentially linking mono- or oligosaccharide groups to a linker-saccharide complex as described above.

These methods are particularly useful for combinatorial synthetic applications. The solid phase or solution phase method of the invention may, for example, be used for combinatorial synthesis of aminoglycoside compounds. It will be appreciated that the sequential linkage may be effected either enzymically or by chemical means.

The invention also provides a kit for solid phase synthesis, solution phase synthesis, or combinatorial synthesis of oligosaccharides, comprising a linker-saccharide complex or a resin-linker-saccharide support according to the invention, as described above. The kit may optionally also comprise one or more further reagents such as partially or differentially activated, fully protected saccharides, protecting agents, deprotecting agents, resins and/or solvents suitable for solid phase or combinatorial synthesis. The person skilled in the art will be aware of suitable further reagents. Different types of kit can then be chosen according to the desired use.

For the purposes of this specification it will be clearly understood that the word "comprising" means "including but not limited to", and that the word "comprises" has a corresponding meaning.

DETAILED DESCRIPTION OF THE INVENTION

Abbreviations used herein are as follows:
Ac acetyl
Bu butyl
Dde N-1-(4,4-Dimethyl-2,6-dioxocyclohexylidene)ethyl
DMF N,N'-Dimethylformamide
EtOH Ethanol
FAB-MS Fast atom bombardment mass spectrometry
Me Methyl
MeOH Methanol
Nde 1-(4-Nitro-1,3-dioxoindan-2-ylidene)ethyl
NHNde NH-1-(4-nitro-1,3-dioxoindan-2-ylidene)ethyl
NMR Nuclear magnetic resonance
ODmab 4-{N-[1-(4,4-dimethyl-2,6-dioxocyclohexylidene)-3-methylbutyl]-amino}benzyl alcohol
SPPS solid phase peptide synthesis
TBDMS tert-butyl dimethyl silyl
tBu tert-butyl
Trt trityl The invention will now be described in detail by way of reference only to the following non-limiting examples, in which the structures of individual compounds are as summarised in the following tables.

TABLE 1

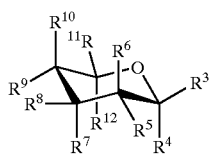

| Compound No. | R³ | R⁴ | R⁵ | R⁶ | R⁷ | R⁸ | R⁹ | R¹⁰ | R¹¹ | R¹² |
|---|---|---|---|---|---|---|---|---|---|---|
| 1 | OH/H | OH/H | NHDde | H | H | OH | OH | H | CH₂OH | H |
| 2 | H | AcO | NHDde | H | H | OAc | OAc | H | CH₂Oac | H |
| 3 | H | Br | NHDde | H | H | OAc | OAc | H | CH₂Oac | H |
| 4 | H/OMe | OMe/H | NHDde | H | H | OAc | OAc | H | CH₂Oac | H |
| 5 | Isothiouronium salt | H | NHDde | H | H | OAc | OAc | H | CH₂Oac | H |
| 6 | SMe | H | NHDde | H | H | OAc | OAc | H | CH₂Oac | H |
| 7 | H | OBn | NHDde | H | H | OH | OH | H | CH₂OH | H |
| 8 | N₃ | H | NHDde | H | H | OAc | Oac | H | CH₂Oac | H |
| 9 | SH | H | NHDde | H | H | OAc | Oac | H | CH₂Oac | H |
| 10 | H | OBn | NHDde | H | H | OH | Benzylidine | H | Benzylidine | H |
| 11 | H | OBn | NHDde | H | H | OAc | Oac | H | CH₂Oac | H |
| 12 | OH/H | H/OH | NHDde | H | H | OAc | Oac | H | CH₂Oac | H |
| 13 | Imidate/H | H/Imidate | NHDde | H | H | OAc | Oac | H | CH₂Oac | H |
| 14 | H | OBn | NHDde | H | H | OH | OH | H | CH₂Otrt | H |
| 15 | H | OBn | NHDde | H | H | OH | OH | H | CH₂OTBDMS | H |
| 16 | NH₂ | H | NHDde | H | H | OAc | Oac | H | CH₂Oac | H |
| 17 | OAc | H | NHDde | H | H | OAc | Oac | H | CH₂Odmab | H |
| 18 | NH₂ | H | NHDde | H | H | OAc | Oac | H | CH₂Oac | H |
| 19 | NHDde | H | NHAc | H | H | OAc | Oac | H | CH₂Oac | H |
| 20 | H | OBn | NHDde | H | H | OH | Isopropylidene | H | Isopropylidene | H |
| 21 | H/OH | OH/H | NHDde | H | H | OH | H | OH | CH₂OH | H |
| 22 | H/OH | OH/H | NHNde | H | H | OH | OH | H | CH₂OH | H |
| 23 | H | OAc | NHNde | H | H | OAc | OAc | H | CH₂Oac | H |

TABLE 2

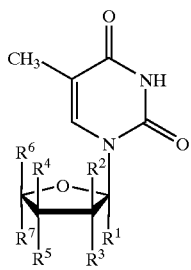

| Compound No. | R¹ | R² | R³ | R⁴ | R⁵ | R⁶ | R⁷ |
|---|---|---|---|---|---|---|---|
| 24 | H | H | H | H | NHDde | CH₂OH | H |

TABLE 3

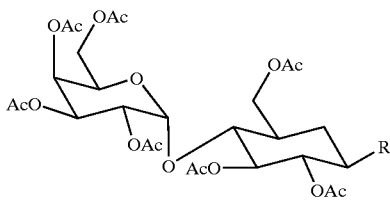

| Compound No. | R |
|---|---|
| 25 | N₃ |
| 26 | NH₂ |
| 27 | NHDde |

EXAMPLE 1

Synthesis of Dde Protected Aminosugars

2-Deoxy-2-[1-(4,4-dimethyl-2,6-dioxo-cyclohex-1-ylidene)ethylamino]-D-glucopyranose (1)

Sodium (143 mg, 6.21 mmol) was added to abs. methanol (30 ml) and the reaction mixture was stirred for 5 min. D-glucosamine hydrochloride (1.34 g., 6.21 mmol) was added to the resulting clear solution and the reaction mixture was stirred at room temperature for another 5 min. 2-Acetyldimedone (1.69 g, 9.32 mmol) was added and the reaction mixture was stirred under reflux for 5 hours. The reaction mixture was cooled and the product was precipitated by ether (200 ml) resulting in 2-Deoxy-2-[1-(4,4-dimethyl-2,6-dioxocyclohex-1-ylidene)-ethylamino]-D-glucopyranose (1) (1.66 g, 77.9%).

$R_f$ 0.37 (MeCN/H₂O 10:0.5);

FAB MS $C_{16}H_{25}NO_7$ (343.33) m/z (%) 366 [M+Na]⁺ (100), 268 (40), 246 (32), 224 (15).

¹H NMR (D₂O) δ5.12 (d, H-1β), 3.95–3.25 (m, 6H, sugar H), 2.38, 2.36 (2s, 3H, CH₃), 2.28, 2.27 (2s, 4H, 2 CH₂), 0.85 (s, 6H, 2 CH₃).

EXAMPLE 2

Synthesis of Dde-protected O-acylated Aminosugars

2-Deoxy-2-[1-(4,4-dimethyl-2,6-dioxocyclohex-1-ylidene)-ethylamino]-1,3,4,6-tetra-O-acetyl-α-D-glucopyranose (2)

A mixture of 2-deoxy-2-[1-(4,4-dimethyl-2,6-dioxocyclohex-1-ylidene)ethyl-amino]-D-glucopyranose (1.55 g, 4.51 mmol), pyridine (11 ml) and acetic anhydride (20 ml) was stirred at room temperature overnight. The reaction mixture was evaporated, and the product was crystallised from MeOH (10 ml) at −15° C. to give 2-Deoxy-2-[1-(-4,4-dimethyl-2,6-dioxocyclohex-1-ylidene)ethylamino]-1,3,4,6-tetra-O-acetyl-α-D-glucopyranose (2) (1.95 g, 86%).

$R_f$ 0.35 (Hexane/EtOAc 1:1);

FAB MS $C_{24}H_{33}NO_{11}$ (511.50) m/z (%) 534 [M+Na]$^+$ (20), 512 [M+H]$^+$ (100), 452 (72), 338 (75).

$^1$H NMR (CDCl$_3$) δ13.70 (d, 1H, NH), 6.22 (d, 1H, H-1, $J_{1,2}$=3.66 Hz), 5.40 (t, 1H, H-3), 5.16 (t, 1H, H-4), 4.36 (dd, 1H, H-6'), 4.25 (m, 1H, H-5), 4.13 (dd, 1H, H-2), 4.05 (dd, 1H, H-6), 2.58 (s, 3H, CH$_3$), 2.35 (s, 4H, 2 CH$_2$), 2.09, 2.03, 1.97 (3s, 9H, 3 AcO), 1.00 (s, 6H, 2 CH$_3$).

EXAMPLE 3

Synthesis of Dde-protected Halogenated Amino Sugars

2-Deoxy-2-[1-(4,4-dimethyl-2,6-dioxocyclohex-1-ylidene)-ethylamino]-3,4,6-tri-O-acetyl-α-D-glucopyranosyl bromide (3)

A mixture of 2-Deoxy-2-[1-(4,4-dimethyl-2,6-dioxocyclohex-1-ylidene)ethylamino]-1,3,4,6-tetra-O-acetyl-α-D-glucopyranose (100 mg, 0.19 mmol) and HBr in acetic acid (45%) (1.0 ml) was stirred at room temperature for 30 min. The reaction mixture was diluted with cold CH$_2$Cl$_2$ (10 ml), washed twice with cold H$_2$O (30 ml), saturated NaHCO$_3$ solution (20 ml) and with H$_2$O again (20 ml). The organic phase was dried over MgSO$_4$ and evaporated, giving 2-Deoxy-2-[1-(4,4-dimethyl-2,6-dioxocyclohex-1-ylidene)-ethylamino]-3,4,6-tri-O-acetyl-α-D-glucopyranosyl bromide (3) (95 mg, 91%).

$R_f$ 0.35 (Hexane/EtOAc 1:1);

FAB MS $C_{22}H_{30}BrNO_9$ (532.37) m/z (%) 534 [M+H]$^+$ (100), 452 (45), 441 (42), 338 (77).

$^1$H NMR (CDCl$_3$) δ13.83 (d, 1H, NH), 6.41 (d, 1H, H-1, $J_{1,2}$=3.65 Hz), 5.52 (t, 1H, H-3), 5.20 (t, 1H, H-4), 4.38 (m, 2H, H-6', H-2), 4.24 (m, 1H, H-5), 4.14 (dd, 1H, H-6), 2.62 (s, 3H, CH$_3$), 2.41 (s, 4H, 2 CH$_2$), 2.11, 2.04, 1.96 (3s, 9H, 3 AcO), 1.02 (s, 6H, 2 CH$_3$)

EXAMPLE 4

Synthesis of Dde-protected O-alkylated Aminosugars

Methyl 2-Deoxy-2-[1-(4,4-dimethyl-2,6-dioxocyclohex-1-ylidene)ethylaminol-]3,4,6-tri-O-acetyl-β-D-glucopyranoside (4)

2-Deoxy-2-[1-(4,4-dimethyl-2,6-dioxocyclohex-1-ylidene)ethylamino]-3,4,6-tri-O-acetyl-α-D-glucopyranosyl bromide (60 mg, 0.11 mmol) was dissolved in CH$_2$C12 (5 ml), cooled to −15° C. and silver trifluoromethanesulphonate (43 mg, 0.16 mmol) in MeOH (1 ml) added. The reaction mixture was stirred overnight, filtered and the filtrate evaporated. The residue was washed with saturated NaHCO$_3$ solution, dried over MgSO$_4$ and evaporated. The residue was purified by chromatography, to give Methyl 2-Deoxy-2-[1-(4,4-dimethyl-2,6-dioxocyclohex-1-ylidene)ethylamino]-3,4,6-tri-O-acetyl-β-D-glucopyranoside (4) (40 mg, 75%).

$R_f$ 0.35 (Hexane/EtOAc 1:1);

FAB MS $C_{23}H_{33}NO_{10}$ (483.49) m/z (%) 506 [M+Na]$^+$ (15), 484 [M+H]$^+$ (100), 442 (8).

$^1$H NMR (CDCl$_3$) δ13.84 (d, 1H, NH), 5.20 (t, 1H, H-3), 5.09 (t, 1H, H-4), 4.41 (d, 1H, H-1, $J_{1,2}$=8.29 Hz), 4.32 (dd, 1H, H-2), 4.14, 3.94 (2m, 2H, H-6), 3.75 (m, 1H, H-5), 3.48 (s, 3H, OCH$_3$), 2.57 (s, 3H, CH$_3$), 2.37 (s, 4H, 2 CH$_2$), 2.09, 2.03, 1.96 (3s, 9H, 3 AcO), 1.02 (s, 6H, 2 CH$_3$),and Methyl 2-Deoxy-2-[1-(4,4-dimethyl-2,6-dioxocyclohex-1-ylidene)ethylamino]-3,4,6-tri-O-acetyl-α-D-glucopyranoside (4a) (3 mg. 6%)

$R_f$ 0.33 (Hexane/EtOAc 1:1);

FAB MS $C_{23}H_{33}NO_{10}$ (483.49) m/z (%) 506 (M+Na]$^+$ (13), 484 [M+H$^+$ (100).

$^1$H NMR (CDCl$_3$) δ13.55 (d, 1H, NH), 5.40 (t, 1H, H-3), 5.08 (t, 1H, H-4), 4.82 (d, 1H, H-1, $J_{1,2}$=3.37 Hz), 4.32 (dd, 1H, H-2), 4.12 (m, 3H, H-6, H-5), 3.53 (s, 3H, OCH$_3$), 2.58 (s, 3H, CH$_3$), 2.41 (s, 4H, 2 CH$_2$), 2.11, 2.02, 1.94 (3s, 9H, 3 AcO), 1.02 (s, 6H, 2 CH$_3$).

EXAMPLE 5

Synthesis of Dde-protected Aminosugar Uronium Salts

S-[2-Deoxy-2-[1-(4,4-dimethyl-2,6-dioxocyclohex-1-ylidene)-ethylamino]-3,4,6-tri-O-acetyl-β-D-glucopyranosyl]-isothiouronium bromide (5)

Thiourea (14 mg, 0.18 mmol) was added to a solution of 2-Deoxy-2-[1-(4,4-dimethyl-2,6-dioxocyclohex-1-ylidene) ethylamino]-3,4,6-tri-O-acetyl-α-D-glucopyranosyl bromide (100 mg, 0.18 mmol) in acetone (0.5 ml). The mixture was refluxed for 15 min then evaporated. The residue was purified by chromatography using CHCl$_3$/MeOH 5:1 as the mobile phase to give S-[2-Deoxy-2-[1-(4,4-dimethyl-2,6-dioxocyclohex-1-ylidene)ethylamino]-3,4,6-tri-O-acetyl-β-D-gluco-pyranosyl]isothiouronium bromide (5).

$R_f$ 0.46 (CHCl$_3$/MeOH 5:1);

FAB MS $C_{23}H_{34}N_3O_9S$ (608.42) m/z (%) 528 [M−Br]$^+$ (20), 452 (100).

$^1$H NMR (CDCl$_3$) δ13.85 (d, 1H, NH), 5.30 (t, 1H, H-3), 5.12 (t, 1H, H-4), 4.75 (d, 1H, H-1, $J_{1,2}$=9.43 Hz), 2.62 (s, 3H, CH$_3$), 2.36 (s, 4H, 2 CH$_2$), 2.11, 2.04, 1.96 (3s, 9H, 3 AcO), 1.02 (s, 6H, 2 CH$_3$).

EXAMPLE 6

Synthesis of Dde-protected Alkylthiolated Aminosugars

Methyl 2-Deoxy-2-[1-(4,4-dimethyl-2,6-dioxocyclohex-1-ylidene)ethylamino]-1-thio-3,4,6-tri-O-acetyl-β-D-glucopyranoside (6)

2-Deoxy-2-[1-(4,4-dimethyl-2,6-dioxocyclohex-1-ylidene)ethylamino]-1-thio-3,4,6-tri-O-acetyl-β-D-glucopyranose (72 mg, 0.148 mmol) was dissolved in acetone (0.15 ml) and K$_2$CO$_3$ (23 mg) in water (0.15 ml) added. The reaction mixture was stirred under N$_2$ at room temperature and methyliodide (23 mg, 0.163 mmol) added. After 30 min stirring the reaction mixture was concentrated under reduced pressure. CH$_2$Cl$_2$ (2 ml) was added to the reaction mixture and the layers were separated. The organic phase was washed with water (0.5 ml), dried over MgSO$_4$ and evaporated. The residue was purified by chromatography using EtOAc/hexane 3:1 to give Methyl 2-Deoxy-2-[1-(4,4-dimethyl-2,6-dioxocyclohex-1-ylidene)ethylamino]-1-thio-3,4,6-tri-O-acetyl-β-D-glucopyranoside (6) (50 mg, 67%).

$R_f$ 0.41 (EtOAc/hexane 3:1);

FAB MS $C_{23}H_{33}NO_9S$ (499.49) m/z (%) 522 [M+Na]$^+$ (25), 500 [M+H]$^+$ (100), 452 (27), 338 (35).

$^1$H NMR (CDCl$_3$) δ13.96 (d, 1H, NH), 5.22 (t, 1H, H-3), 5.13 (t, 1H, H-4), 4.61 (d, 1H, H-1, $J_{1,2}$=9.98 Hz), 4.30 (dd, 1H, H-2), 4.15 (m, 2H, H-6', H-5), 2.60 (s, 3H, CH$_3$), 2.42 (s, 4H, 2 CH$_2$), 2.20 (s, 3H, SCH$_3$), 2.09, 2.02, 1.96 (3s, 9H, 3 AcO), 1.03 (s, 6H, 2 CH$_3$).

EXAMPLE 7

Synthesis of Dde-protected Benzylated Aminosugars

Benzyl 2-Deoxy-2-[1-(4,4-dimethyl-2,6-dioxocyclohex-1-ylidene)ethylamino]-α-D-glucopyranoside (7)

A solution of Benzyl 2-Acetamido-2-deoxy-α-D-glucopyranoside (4.70 g, 15.11 mmol) in 1 M NaOH solution was refluxed at 120° C. for 15 h. The reaction mixture was cooled to room temperature, neutralised with 1 M HCl solution and concentrated. The residue was dissolved in dry ETOH (50 ml) and filtered. 2-Acetyldimedone (4.11 g, 22.6 mmol) and N,N-diisopropylethylamine (2 ml) were added to the filtrate, and the mixture was refluxed for 2 h. The reaction mixture was evaporated to dryness, and the residue was taken up in EtOAc (50 ml), washed with 1M KHSO$_4$ solution, brine, and evaporated to give Benzyl 2-Deoxy-2-[1-(4,4-dimethyl-2,6-dioxocyclohex-1-ylidene) ethylamino]-α-D-glucopyranoside (7) (3.78 g, 58%).

$R_f$ 0.43 (CH$_2$Cl$_2$/EtOAc/MeOH 10:7:3);

FAB MS $C_{23}H_{31}NO_7$ (433.48) m/z (%) 456 [M+Na]$^+$ (45), 434 [M+H]$^+$ (100), 452 (30), 338 (25).

$^1$H NMR (CDCl$_3$) δ13.44 (d, 1H, NH), 7.33–7.21 (m, 5H, 5 Ar—H), 4.80 (d, 1H, H-1, $J_{1,2}$=3.45 Hz), 4.71, 4.56 (2d, 2H, CH$_2$Ar), 2.45 (s, 3H, CH$_3$), 2.31 (s, 4H, 2 CH$_2$), 0.99 (s, 6H, 2 CH$_3$).

EXAMPLE 8

Synthesis of Dde-protected Azido Derivative of Aminosugars

2-Deoxy-2-[1-(4,4-dimethyl-2,6-dioxocyclohex-1-ylidene)-ethylamino]-3,4,6-tri-O-acetyl-β-D-glucopyranosyl azide (8)

A mixture of 2-Deoxy-2-[1-(4,4-dimethyl-2,6-dioxocyclohex-1-ylidene)ethylamino]-3,4,6-tri-O-β-D-glucopyranosyl bromide (100 mg, 0.18 mmol), sodium azide 100 mg, 1.56 mmol) in DMF (5 ml) was stirred at 80° C. for 2 hours. The reaction mixture was evaporated, taken up in CH$_2$Cl$_2$ (10 ml), washed with H$_2$O (2×2 ml), dried over MgSO$_4$ and concentrated. The residue was purified by chromatography, using hexane/EtOAc 1:1 as the mobile phase, to give 2-Deoxy-2-[1-(4,4-dimethyl-2,6-dioxocyclohex-1-ylidene)ethylamino]-3,4,6-tri-O-acetyl-β-D-glucopyranosyl azide (8) (65 mg, 70%).

$R_f$ 0.55 (hexane/EtOAc 1:1);

FAB MS $C_{22}H_{30}N_4O_9$ (494.48) m/z (%) 517 [M+Na]$^+$ (15), 495 [M+H]$^+$ (100), 452 (10), 338 (25).

$^1$H NMR (CDCl$_3$) δ13.91 (d, 1H, NH), 5.19 (t, 1H, H-3), 5.10 (t, 1H, H-4), 4.87 (d, 1H, H-1, $J_{1,2}$=8.95 Hz), 4.34 (dd, 1H, H-2), 4.15 (dd, 1H, H-6'), 3.85 (m, 2H, H-5, H-6), 2.59 (s, 3H, CH$_3$), 2.38 (s, 4H, 2 CH$_2$), 1.02 (s, 6H, 2 CH$_3$).

EXAMPLE 9

Synthesis of Dde-protected Thiolated Aminosugars

2-Deoxy-2-[1-(4,4-Dimethyl-2,6-dioxocyclohex-1-ylidene)-ethylamino]-1-thio-3,4,6-tri-O-acetyl-β-D-glucopyranose (9)

To S-[2-Deoxy-2-[1-(4,4-dimethyl-2,6-dioxocyclohex-1-ylidene)ethylamino]-3,4,6-tri-O-acetyl-β-D-glucopyranosyl]isothiouronium bromide (136 mg, 0.22 mmol) a solution of Na$_2$S$_2$O$_5$ (43 mg, 0.225 mmol) in water (0.2 ml) and 1,2-dichloroethane (0.24 ml) was added. The reaction mixture was kept under reflux at 85° C. for 20 min. After dilution with CH$_2$Cl$_2$ (5 ml), the layers were separated, the organic phase was washed with water (3 ml), dried over MgSO$_4$, concentrated under reduced pressure, and chromatographed using ether/MeOH 10:1 to give 2-Deoxy-2-[1-(4,4-dimethyl-2,6-dioxocyclohex-1-ylidene)ethylamino]-1-thio-3,4,6-tri-O-acetyl-β-D-glucopyranose (9) (95 mg, 87%).

$R_f$ 0.31 (ether/MeOH 10:1);

FAB MS $C_{22}H_{31}NO_9S$ (485.47) m/z (%) 508 [M+Na]$^+$ (15), 486 [M+H]$^+$ (100), 452 (33), 338 (20).

$^1$H NMR (CDCl$_3$) δ13.97 (d, 1H, NH), 5.32 (t, 1H, H-3), 5.15 (t, 1H, H-4), 4.75 (dd, 1H, H-1, $J_{1,2}$=8.29 Hz), 3.85 (m, 1H, H-5), 2.62 (s, 3H, CH$_3$), 2.38 (s, 4H, 2 CH$_2$), 2.10, 2.04, 1.96 (3s, 9H, 3 AcO), 1.02 (s, 6H, 2 CH$_3$).

EXAMPLE 10

Synthesis of Dde-protected Benzylidene Derivative of Aminosugars

Benzyl 4,6-O-Benzylidene-2-deoxy-2-[1-(4,4-dimethyl -2,6-dioxocyclohex-1-ylidene)ethylamino]-α-D-glucopyranoside (10)

A mixture of benzaldehyde (1 ml), formic acid (1 ml) and Benzyl 2-Deoxy-2-[1-(4,4-dimethyl-2,6-dioxocyclohex-1-ylidene)ethylamino]-α-D-glucopyranoside (433 mg, 1 mmol) was stirred at room temperature for 2 h. The reaction mixture was evaporated to dryness using a high vacuum rotary evaporator. The residue was treated with ether (40 ml) and the suspension filtered. The solid purified by chromatography, using CHCl$_3$-EtOAc 10:4 as the mobile phase, to give Benzyl 4,6-O-Benzylidene-2-deoxy-2-(1-(4, 4-dimethyl-2,6-dioxocyclohex-1-ylidene)-ethylaminol-α-D-glucopyranoside (10) (340 mg, 65%).

$R_f$ 0.38 (CHCl$_3$-EtOAc 10:4);

FAB MS $C_{30}H_{35}NO_7$ (521.58) m/z (%) 544 [M+Na]$^+$ (10), 522 [M+H]$^+$ (100), 338 (40).

$^1$H NMR (CDCl$_3$) δ13.52 (d, 1H, NH), 7.37–7.26 (m, 10H, 10 Ar—H), 5.56 (s, 1H, CH—Ar), 4,90, 4.60 (2d, 2H, CH$_2$—Ar), 4.79 (d, 1H, H-1, $J_{1,2}$=3.08 Hz), 4.35 (t, 1H, H-4), 4.26 (dd, 1H, H-2), 3.98 (m, 2H, H-5, H-3), 3.77 (t, 1H, H-6'), 3.63 (t, 1H, H-6), 2.57 (s, 3H, CH$_3$), 2.33 (s, 4H, 2 CH$_2$), 1.01 (s, 6H, 2 CH$_3$).

EXAMPLE 11

Synthesis of Dde-protected Reducing Aminosugars

2-Deoxy-2-[1-(4,4-dimethyl-2,6-dioxocyclohex-1-ylidene)-ethylamino]-3,4,6-tri-O-acetyl-α-D-glucopyranose (12)

Benzyl 2-Deoxy-2-[1-(4,4-dimethyl-2,6-dioxocyclohex-1-ylidene)ethylamino]-α-D-glucopyranoside (400 mg, 0.92 mmol) was dissolved in pyridine (6 ml) and cooled to 0° C., then acetic anhydride (10 ml) was added dropwise. The solution was stirred at room temperature overnight, then evaporated. The residue was purified by chromatography using EtOAc/hexane 3:1 to give Benzyl 2-Deoxy-2-[1-(4,4-dimethyl-2,6-dioxocyclohex-1-ylidene)-ethylamino]-3,4,6-tri-O-acetyl-α-D-glucopyranoside (11) (465 mg, 90%).

$R_f$ 0.41 (EtOAc/hexane 3:1);

FAB MS $C_{29}H_{37}NO_{10}$ (559.59) m/z (%) 532 [M+Na]$^+$ (15), 560 [M+H]$^+$ (100), 452 (20), 338 (55).

$^1$H NMR (CDCl$_3$) δ13.66 (d, 1H, NH), 7.43–7.32 (m, 5H, 5 Ar—H), 5.45 (t, 1H, H-3), 5.07 (t, 1H, H-4), 4.93 (d, 1H, H-1, $J_{1,2}$=3.53 Hz), 4.76, 4.72 (2d, 2H, CH$_2$—Ar), 4.29 (dd, 1H, H-2), 4.07 (m, 2H, H-6', H-5), 3.96 (dd, 1H, H-6), 2.52 (s, 3H, CH$_3$), 2.38 (s, 4H, 2 CH$_2$), 2.10, 2.00, 1.94 (3s, 9H, 3 AcO), 1.03 (s, 6H, 2 CH$_3$).

Benzyl 2-Deoxy-2-[1-(4,4-dimethyl-2,6-dioxo-cyclohex-1-ylidene)ethylamino]-3,4,6-tri-O-acetyl-α-D-glucopyranoside (11) (100 mg, 0.17 mmol) was dissolved in MeOH (5 ml) and hydrogenated over Pd/C (10%) (20 mg) overnight. The suspension was filtered, and the filtrate was evaporated to give 2-Deoxy-2-[1-(4,4-dimethyl-2,6-dioxocyclohex-1-ylidene)ethylamino]-3,4,6-tri-O-acetyl-α-D-glucopyranose (12) (75 mg, 90%).

$R_f$ 0.44 (CHCl$_3$/EtOAc 1:1);

FAB MS $C_{22}H_{31}NO_{10}$ (469.47) m/z (%) 492 [M+Na]$^+$ (45), 470 [M+H]$^+$ (100), 452 (10).

$^1$H NMR (CDCl$_3$) δ13.81 (d, 1H, NH), 5.49 (t, 1H, H-3), 5.28 (d, 1H, H-1, $J_{1,2}$=3.29 Hz), 5.11 (t, 1H, H-4), 4.42 (dd, H, H-2), 4.33 (dd, H, H-6'), 2.59 (s, 3H, CH$_3$), 2.37 (s, 4H, 2 CH$_2$), 2.10, 2.03, 1.96 (3s, 9H, 3 AcO), 1.01 (s, 6H, 2 CH$_3$).

EXAMPLE 12

Synthesis of Dde-protected Trichloroacetimidate of Aminosugars

2-Deoxy-2-[1-(4,4-dimethyl-2,6-dioxocyclohex-1-ylidene)-ethylamino]-3,4,6-tri-O-acetyl-α,β-D-glucopyranosyl trichloroacetimidate (13)

A mixture of 2-Deoxy-2-[1-(4,4-dimethyl-2,6-dioxocyclohex-1-ylidene)ethylamino]-3,4,6-tri-O-acetyl-α-D-glucopyranose (100 mg, 0.21 mmol) and trichloroacetonitrile in CH$_2$Cl$_2$ was cooled to 0° C. and 1,8-diazabicyclo (5.4.0)undec-7-en (2 mg) added. The reaction mixture was stirred at 0° C. for 1.5 h and at room temperature for 2 h. The solution was evaporated, and the residue chromatographed using CHCl$_3$/EtOAc 1:1 as the mobile phase to give 2-deoxy-2-[1-(4,4-dimethyl-2,6-dioxocyclohex-1-ylidene)ethylamino]-3,4,6-tri-O-acetyl-α,β-D-glucopyranosyl trichloroacetimidate (13) (71 mg, 55%).

$R_f$ 0.61 (CHCl$_3$/EtOAc 1:1);

FAB MS $C_{24}H_{31}Cl_3N_2O_{10}$ (613.88) m/z (%) 635 [M+Na]$^+$ (75), 452 (100).

$^1$H NMR (CDCl$_3$) δ13.95, 13.72 (2d, 1H, NH$_{A}$,β), 8.84, 8.76 (2s, 1H, NH$_{A}$,β), 6.48 (d, H-1$_α$, $J_{1,2}$=3.05 Hz), 5.85 (d, H-1$_β$, $J_{1,2}$=8.72 Hz), 5.52 (t, 1H, H-3), 5.31 (t, 1H, H-4), 2.65, 2.63 (2s, 3H, CH$_{3α,β}$), 2.31 (2s, 4H, 2 CH$_{2α,β}$), 2.09, 2.08, 2.05, 2.04, 1.99, 1.97 (6s, 9H, 3 AcO$_{α,β}$), 0.99, 0.98 (2s, 6H, 2 CH$_{3α,β}$).

EXAMPLE 13

Synthesis of Dde-protected O-triphenylmethylated Aminosugars

Benzyl 2-Deoxy-2-[1-(4,4-dimethyl-2,6-dioxocyclohex-1-ylidene)ethylamino]-6-O-triphenylmethyl-α-D-glucopyranoside (14)

A mixture of Benzyl 2-Deoxy-2-[1-(4,4-dimethyl-2,6-dioxocyclohex-1-ylidene)ethylamino]-α-D-glucopyranoside (100 mg, 0.23 mmol), triphenylmethylbromide (149 mg, 0.46 mmol) in DMF/pyridine 1:1 (2 ml) was stirred at 100° C. for 15 h. The reaction mixture was evaporated, the residue was taken up in CHCl$_3$ (10 ml), washed with water (3 ml), dried over MgSO$_4$ and concentrated. The residue was purified by chromatography using CHCl$_3$/MeOH 10:1 as the mobile phase to give Benzyl 2-Deoxy-2-[1-(4,4-dimethyl-2,6-dioxocyclohex-1-ylidene)ethylamino]-6-O-triphenylmethyl-α-D-glucopyranoside (14) (104 mg, 64%).

$R_f$ 0.55 (CHCl$_3$/MeOH 10:1);

FAB MS $C_{42}H_{45}NO_7$ (675.68) m/z (%) 698 [M+Na]$^+$ (40), 676 [M+H]$^+$ (100).

$^1$H NMR (CDCl$_3$) δ13.49 (d, 1H, NH), 7.49–7.23 (m, 20H, 20 Ar—H), 4.87, 4.66(2d, 2H, CH$_2$Ar), 4.83 (d, 1H, H-1, $J_{1,2}$=3.70 Hz), 3.84 (t, 1H, H-3), 2.55 (s, 3H, CH$_3$), 2.31 (s, 4H, 2 CH$_2$), 1.02 (s, 6H, 2 CH$_3$).

EXAMPLE 14

Synthesis of Dde-protected O-silylated Aminosugars

Benzyl 2-Deoxy-2-[1-(4,4-dimethyl-2,6-dioxocyclohex-1-ylidene)ethylamino]-6-O-t-butyldimethylsilyl-α-D-glucopyranoside (15)

Benzyl 2-Deoxy-2-[1-(4,4-dimethyl-2,6-dioxocyclohex-1-ylidene)ethylamino]-α-D-glucopyranoside (100 mg, 0.23 mmol) was dissolved in dry pyridine (2 ml), cooled to 0° C. and t-butyldimethylsilylchloride (39 mg, 0.26 mmol) added. The reaction mixture was stirred at room temperature overnight. The solution was evaporated, the residue was taken up in CHCl$_3$ (10 ml), washed with water (3 ml), dried over MgSO$_4$ and concentrated. The residue was purified by chromatography using CHCl$_3$/MeOH 10:1 as the mobile phase to give Benzyl 2-Deoxy-2-[1-(4,4-dimethyl-2,6-dioxocyclohex-1-ylidene)ethylamino]-6-O-t-butyldimethylsilyl-α-D-glucopyranoside (15) (77 mg, 61%).

$R_f$ 0.57 (CHCl$_3$/MeOH 10:1);

FAB MS $C_{29}H_{45}NO_7Si$ (547.74) m/z (%) 570 [M+Na]$^+$ (10), 548 [M+H]$^+$ (100).

$^1$H NMR (CDCl$_3$) δ13.45 (d, 1H, NH), 7.40–7.27 (m, 5H, 5 Ar—H), 4.88, 4.65(2d, 2H, CH$_2$Ar), 4.79 (d, 1H, H-1, $J_{1,2}$=3.42 Hz), 2.55 (s, 3H, CH$_3$), 2.31 (s, 4H, 2 CH$_2$), 1.02 (s, 6H, 2 CH$_3$), 0.93 (s, 9H, 3 CH3), 0.10 (s, 6H, 2 CH$_3$Si)

EXAMPLE 15

Synthesis of Partially Protected Polyaminosugars

2-Deoxy-2-[1-(4,4-dimethyl-2,6-dioxocyclohex-1-ylidene)-ethylamino]-3,4,6-tri-O-acetyl-β-D-glucopyranosyl amine (16)

2-Deoxy-2-[1-(4,4-dimethyl-2,6-dioxocyclohex-1-ylidene)ethylamino]-3,4,6-tri-O-acetyl-β-D-glucopyranosyl amine (60 mg, 0.12 mmol) was dissolved in MeOH (5 ml) and hydrogenated over Pd/C (10%) (10 mg) overnight. The suspension was filtered, the filtrate was evaporated to give 2-Deoxy-2-[1-(4,4-dimethyl-2,6-dioxocyclohex-1-ylidene)ethylamino]-3,4,6-tri-O-acetyl-β-D-glucopyranosyl amine (16) (45 mg, 80%).

$R_f$ 0.38 (EtOAc);

FAB MS $C_{22}H_{32}N_2O_9$ (468.50) m/z (%) 491 [M+Na]$^+$ (100), 469 [M+H]$^+$ (25), 452 (10).

¹H NMR (CDCl₃) δ13.75 (d, 1H, NH), 2.61 (s, 3H, CH₃), 2.35 (s, 4H, 2 CH₂), 2.09, 2.02, 1.98 (3s, 9H, 3 AcO), 1.03 (s, 6H, 2 CH₃).

EXAMPLE 16

Synthesis of Dmab-protected Sugars

4-[N-[1-(4,4-dimethyl-2,6-dioxocyclohexylidene)-ethyl]-amino]benzyl (1,2,3,4-tetra-O-acetyl-β-D-glucopyranose)uronate (17)

A mixture of 1,2,3,4-tetra-O-acetyl-β-D-glucuronic acid (100 mg, 0.27 mmol), 4-[N-[1-(4,4-dimethyl-2,6-dioxocyclohexylidene)ethyl]amino]benzyl alcohol (79 mg, 0.27 mmol), 1,3-dicyclohexylcarbodiimide (62 mg, 0.30 mmol) in CH₂Cl₂ was stirred overnight at room temperature. The reaction mixture was evaporated, the residue was purified by chromatography using CHCl₃/EtOAc 10:4 to give 4-[N-[1-(4,4-dimethyl-2,6-dioxocyclohexylidene)ethyl]-amino]benzyl (1,2,3,4-tetra-O-acetyl-β-D-glucopyranose) uronate (17) (92 mg, 53%).

$R_f$ 0.51 (CHCl₃/EtOAc 10:4);

FAB MS $C_{31}H_{37}NO_{13}$ (631.61) m/z (%) 654 [M+Na]⁺ (10), 632 [M+H]⁺ (35), 270 (100).

¹H NMR (CDCl₃) δ15.06 (d, 1H, NH), 7.41 (d, 2H, 2 Ar—H), 7.15 (d, 2H, 2 Ar—H), 5.76 (d, 1H, H-1, $J_{1,2}$=9.08 Hz), 4.22 (d, 1H, H-5, $J_{1,2}$=9.36 Hz), 2.51 (s, 3H, CH₃), 2.37 (s, 4H, 2 CH₂), 2.09, 2.00, 1.86 (3s, 9H, 3 AcO), 1.07 (s, 6H, 2 CH₃).

EXAMPLE 17

Synthesis of Dde- and N-acyl-protected Polyaminosugars

2-Acetamido-3,4,6-tri-O-acetyl-1,2-dideox-1-[1-(4,4-dimethyl-2,6-dioxocyclohex-1-ylidene)ethyamino]-β-D-glucopyranose (19)

2-Acetamido-2-deoxy-3,4,6-tri-O-acetyl-β-D-glucopyranosyl azide (100 mg, 0.26 mmol) was dissolved in MeOH (5 ml) and hydrogenated over Pd/C (10%) (10 mg) for 5 h. The suspension was filtered, and the filtrate was evaporated to give 2-Acetamido-2-deoxy-3,4,6-tri-O-acetyl-β-D-glucopyranosyl amine (18) (80 mg, 86%).

$R_f$ 0.38 (CHCl₃/MeOH 10:1);

FAB MS $C_{14}H_{22}N_2O_8$ (346.34) m/z (%) 347 [M+H]⁺ (100), 330 (25).

¹H NMR (CDCl₃) δ5.64 (d, 1H, NH), 3.99 (m, 1H, H-2), 3.65 (m, 1H, H-5), 2.11, 2.04, 2.02, 1.97 (4s, 12H, 3 AcO, AcNH).

A mixture of 2-Acetamido-2-deoxy-3,4,6-tri-O-acetyl-β-D-glucopyranosyl amine (80 mg, 0.23 mmol) and 2-acetyldimedone (55 mg, 0.30 mmol) in MeOH (5 ml) was refluxed for 5 h. The reaction mixture was evaporated, the residue was purified by chromatography using CHCl₃/MeOH 10:0.5 as the mobile phase, to give 2-Acetamido-3,4,6-tri-O-acetyl-1,2-dideoxy-1-[1-(4,4-dimethyl-2,6-dioxocyclohex-1-ylidene)ethylamino]-β-D-glucopyranose (19) (70 mg, 60%).

$R_f$ 0.37 (CHCl₃/MeOH 10:0.5);

FAB MS $C_{24}H_{34}N_2O_{10}$ (510.53) m/z (%) 533 [M+Na]⁺ (80), 511 [M+H]⁺ (100), 330 (25).

¹H NMR (CDCl₃) δ13.60 (d, 1H, NH), 5.81 (d, 1H, NH), 5.45 (t, 1H, H-3), 5.31 (m, 1H, H-1), 5.05 (t, 1H, H-4), 4.21 (dd, 1H, H-6'), 4.11 (dd, 1H, H-6), 3.92 (m, 1H, H-2), 3.82 (m, 1H, H-5), 2.58 (s, 3H, CH3), 2.35 (s, 4H, 2 CH₂), 2.06, 2.04, 2.02, 1.92 (3s, 9H, 2 AcO, AcNH), 1.01 (s, 6H, 2 CH₃).

EXAMPLE 18

Synthesis of Dde-protected O-isopropylidene Derivative of Aminosugars

Benzyl 2-Deoxy-2-[1-(4,4-dimethyl-2,6-dioxocyclohex-1-ylidene)ethylamino]-4,6-O-isopropylidene-α-D-glucopyranoside (20)

A mixture of Benzyl 2-Deoxy-2-[1-(4,4-dimethyl-2,6-dioxocyclohex-1-ylidene)ethylamino]-α-D-glucopyranoside (100 mg, 0.23 mmol) and (+/−)-10-camphorsulphonic acid (5 mg) in 2,2-dimethoxypropane (10 ml) was refluxed for 2 h. The reaction mixture was evaporated, and the residue was taken up in CH₂Cl₂ (10 ml), washed with saturated NaHCO₃ solution (3 ml), and concentrated. The residue was purified by chromatography using CH₂Cl₂/MeOH 10:1 as the mobile phase to give Benzyl 2-Deoxy-2-[1-(4,4-dimethyl-2,6-dioxocyclohex-1-ylidene)ethylamino]-4,6-O-isopropylidene-α-D-glucopyranoside (20) (82 mg, 75%).

$R_f$ 0.44 (CH₂Cl₂/MeOH 10:1);

FAB MS $C_{26}H_{35}NO_7$ (473.54) m/z (%) 496 [M+Na]⁺ (20), 474 [M+H]⁺ (100), 382 (15).

¹H NMR (CDCl₃) δ13.48 (d, 1H, NH), 7.38–7.27 (m, 5H, 5 Ar—H), 4.97, 4.65(2d, 2H, CH₂Ar), 4.76 (d, 1H, H-1, $J_{1,2}$=3.55 Hz), 2.55 (s, 3H, CH₃), 2.31 (s, 4H, 2 CH₂), 1.52, 1.30 (2s, 6H, 2 CH₃), 1.00 (s, 6H, 2 CH₃).

EXAMPLE 19

Synthesis of Dde-protected Galactoaminosugars

2-Deoxy-2-[1-(4,4-dimethyl-2,6-dioxocyclohex-1-ylidene)-ethylamino]-D-galactcopyranose (21)

Sodium (22 mg, 0.95 mmol) was added to abs. methanol (10 ml) and the reaction mixture was stirred for 5 min. D-galactosamine hydrochloride (206 mg, 0.95 mmol) was added to the resulting clear solution, and the reaction mixture was stirred at room temperature for another 5 min. 2-Acetyldimedone (261 mg, 1.43 mmol) was added and the reaction mixture was stirred under reflux for 5 hours. The solution was cooled and the product was precipitated by ether (100 ml) resulting in 2-Deoxy-2-[1-(4,4-dimethyl-2,6-dioxocyclohex-1-ylidene)ethylamino]-D-galactopyranose (21) (270 mg, 75%).

$R_f$ 0.37 (MeCN/H₂O 10:0.5);

FAB MS $C_{16}H_{25}NO_7$ (343.33) m/z (%) 366 [M+Na]⁺ (40), 344 [M+H]⁺ (100), 327 (30).

¹H NMR (D₂O) δ5.34 (d, H-1$_A$, $J_{1,2}$=3.54 Hz), 4.87 (d, H-1$_β$), 4.28 (dd, H-2$_α$), 4.17 (t, H-2$_β$), 4.08 (d, H4$_α$), 4.03 (d, H-4$_β$), 2.56 (s, 3H, CH₃), 2.48, 2.44 (2s, 4H, 2 CH₂), 1.03 (s, 6H, 2 CH₃).

EXAMPLE 20

Synthesis of Nde-protected Aminosugars

2-Deoxy-2-[1-(4-nitro-1,3-dioxoindan-2-ylidene)-ethylamino]-D-glucopyranose (22)

Sodium (126 mg, 5.47 mmol) was added to abs. methanol (50 ml) and the reaction mixture was stirred for 5 min. D-glucosamine hydrochloride (1.18 g, 5.47 mmol) was added to the resulting clear solution and the reaction mixture was stirred at room temperature for another 5 min. 2-acetyl-4-nitroindane-1,3-dion (1.91 g, 8.21 mmol) was added and the reaction mixture was stirred under reflux for 5 hours. The solution was cooled and the product was filtered off. The solid was washed with MeOH (10 ml), ether (50 ml) and dried, affording 2-Deoxy-2-[1-(4-nitro-1,3-dioxoindan-2-ylidene)ethylamino]-D-glucopyranose (22) 1.10 g, 55%).

$R_f$ 0.41 (MeCN/$H_2O$ 10:0.5);

FAB MS $C_{17}H_{18}N_2O_9$ (394.32) m/z (%) 395 [M+H]$^+$ (100).

$^1$H NMR ($D_2O$) δ7.75–7.40 (m, 3H, 3 Ar—H), 5.21 (d, H-1$_\alpha$), 3.95–3.25 (sugar 6H), 3.18 (s, 3H, $CH_3$).

EXAMPLE 21

Synthesis of Nde-protected O-acetylated Aminosugars

2-Deoxy-2-[1-(4-nitro-1,3-dioxoindan-2-ylidene)-ethylamino]-3,4,6-tri-O-acetyl-α-D-glucopyranose (23)

A mixture of 2-Deoxy-2-[1-(4-nitro-1,3-dioxoindan-2-ylidene)ethylamino]-D-glucopyranose (100 mg, 0.23 mmol), pyridine (2 ml) and acetic anhydride (3 ml) stirred at room temperature overnight. The reaction mixture was evaporated, and the residue was purified by chromatography using $CHCl_3$/EtOAc 10:4 as the mobile phase to give 2-Deoxy-2-[1-(4-nitro-1,3-dioxoindan-2-ylidene)-ethylamino]-3,4,6-tri-O-acetyl-α-D-glucopyranose (23) (165 mg, 79%).

FAB MS $C_{25}H_{26}N_2O_{13}$ (562.48) m/z (%) 585 [M+Na]$^+$ (40), 563 [M+H]$^+$ (100), 503 (45).

$^1$H NMR ($CDCl_3$) δ11.00, 10.90 (2d, 1H, NH$_{E,Z}$), 7.95–7.68 (m, 3H, 3 Ar—H), 6.25, 6.24 (2d, 1H, H-1$_{E,Z}$), 5.43 (t, 1H, H-3), 5.18 (t, 1H, H-4), 2.68 (s, 3H, $CH_3$), 2.38, 2.07, 2.04, 2.00 (4s, 12H, 4 AcO).

EXAMPLE 22

Synthesis of Dde-protected Deoxyaminosugars with Furanose Ring

3'-deoxy-3'-[1-(4,4-dimethyl-2,6-dioxocyclohex-1-ylidene)-ethylamino]-thymidine (24)

3'-Deoxy-3'-azido-thymidine (200 mg, 0.75 mmol) was dissolved in MeOH (25 ml) and Pd/C (40 mg) was added. The suspension was stirred over a constant stream of $H_2$ overnight. The reaction mixture was filtered, and the filtrate was concentrated. The residue was taken up in abs. EtOH (5 ml), N,N-diisopropylethylamine (0.1 ml) and 2-acetyldimedone (204 mg, 1.12 mmol) were added and the solution was refluxed for 5 h. The reaction mixture was cooled to room temperature and the product was precipitated by adding ether (50 ml) giving 3'-deoxy-3'-[1-(4,4-dimethyl-2,6-dioxocyclohex-1-ylidene)-ethylamino]-thymidine (24) (200 mg, 66%).

$R_f$ 0.45 ($CH_2Cl_2$/EtOAc/MeOH 10:7:3);

FAB MS $C_{20}H_{27}N_3O_4$ (405.45) m/z (%) 428 [M+Na]$^+$ (55), 406 [M+H]$^+$ (100).

$^1$H NMR ($CDCl_3$) δ13.79 (d, 1H, NH), 7.55 (s, 1H, H-6), 6.13 (m, 1H, H-1'), 4.70 (m, 1H, H-5'), 4.04 (m, 1H, H-3'), 3.96 (dd, 1H, H-5'$_a$), 3.72 (dd, 1H, H-5'$_b$), 2.55 (s, 3H, $CH_3$), 2.42 (m, 1H, H-2'$_a$), 2.32 (s, 4H, 2 $CH_2$), 1.80 (s, 3H, $CH_3$), 0.96 (s, 6H, 2 $CH_3$).

EXAMPLE 23

Synthesis of Dde-protected Aminosugar Containing Oligosaccharides

4-O-(2,3,4,6-tetra-O-acetyl-α-D-galactopyranosyl)-2,3,6-tri-O-acetyl-N-[1-(4,4-dimethyl-2,6-dioxocyclohex-1-ylidene)ethyl]-β-D-glucopyranosyl amine (27)

A mixture of β-lactose octaacetate (203 mg, 0.3 mmol), trimethylsilyl azide (41 mg, 0.35 mmol), and $SnCl_4$ (40 mg, 0.15 mmol) in $CH_2Cl_2$ (1.5 ml) was stirred overnight at room temperature. The solution was diluted with $CH_2Cl_2$ (20 ml) and washed twice with 1 M potassium fluoride solution (5 ml), water (5 ml) and evaporated affording 4-O-(2,3,4,6-tetra-O-acetyl-α-D-galactopyranosyl)-2,3,6-tri-O-acetyl-β-D-glucopyranosyl azide (25) (178 mg 90%).

$R_f$ 0.38 (hexane/EtOAc 1:1);

FAB MS $C_{26}H_{35}N_3O_{17}$ (661.56) m/z (%) 684 [M+Na]$^+$ (70), 662 [M+H]$^+$ (20), 331 (100).

$^1$H NMR ($CDCl_3$) δ5.35 (d, 1H, H-4'), 4.95 (d, 1H, H-1', $J_{1,2}$=3.63 Hz), 4.61 (d, 1H, H-1, $J_{1,2}$=9.13 Hz), 2.14, 2.13, 2.07, 2.06, 2.04, 1.96 (6s, 21H, 7 AcO).

4-O-(2,3,4,6-tetra-O-acetyl-α-D-galactopyranosyl)-2,3,6-tri-O-acetyl-β-D-glucopyranosyl azide (178 mg, 0.26 mmol) was dissolved in MeOH (5 ml) and hydrogenated over Pd/C (10%) (10 mg) for 5 h. The suspension was filtered, and the filtrate was evaporated to give 4-O-(2,3,4,6-tetra-O-acetyl-α-D-galacto-pyranosyl)-2,3,6-tri-O-acetyl-β-D-glucopyranosyl amine (26) (157 mg, 92%).

$R_f$ 0.41 (EtOAc);

FAB MS $C_{26}H_{37}NO_{17}$ (635.56) m/z (%) 658 [M+Na]$^+$ (35), 636 [M+H]$^+$ (40), 331 (100).

$^1$H NMR ($CDCl_3$) δ5.35 (d, 1H, H-4'), 2.15, 2.12, 2.07, 2.06, 2.04, 2.03, 1.96 (7s, 21H, 7 AcO).

A mixture of 4-O-(2,3,4,6-tetra-O-acetyl-α-D-galactopyranosyl)-2,3,6-tri-O-acetyl-β-D-glucopyranosyl amine (157 mg, 0.24 mmol) and 2-acetyldimedone (81 mg, 0.45 mmol) in MeOH (5 ml) was refluxed for 5 h. The reaction mixture was evaporated, and the residue was purified by chromatography using $CHCl_3$/EtOAc 1:1 as the mobile phase, to give 4-O-(2,3,4,6-tetra-O-acetyl-α-D-galactopyranosyl)-2,3,6-tri-O-acetyl-N-[1-(4,4-dimethyl-2,6-dioxocyclohex-1-ylidene)ethyl]-β-D-glucopyranosyl amine (27) (106 mg, 54%).

$R_f$ 0.39 ($CHCl_3$/EtOAc 1:1);

FAB MS $C_{36}H_{49}NO_{19}$ (799.75) m/z (%) 822 [M+Na]$^+$ (50), 800 [M+H]$^+$ (100).

$^1$H NMR ($CDCl_3$) δ13.56 (d, 1H, NH), 5.35 (d, 1H, H-1', $J_{1,2}$=3.13 Hz), 2.60 (s, 3H, $CH_3$), 2.36 (s, 4H, 2 $CH_2$), 2.15, 2.12, 2.07, 2.06, 2.04, 2.03, 1.96 (7s, 21H, 7 AcO), 1.02 (s, 6H, 2 $CH_3$).

EXAMPLE 24

Synthesis of 2-Acetyl-4-nitroindan-1,3-dione

2-Acetyl-4-nitroindan-1,3-dione

A mixture of 3-nitrophthalic anydride (12 g, 60 mmol), anhydrous pyridine (25 ml), piperidine (0.2 ml) and 2,4-pentanedione (6.25 g, 60 mmol) was stirred at 40° C. for 6 h. The reaction mixture was cooled to 0° C. and the crystalline mass was collected at the pump, washed with ether, and dried to give the yellow pyridinium salt. The salt was treated with 6 M HCl (100 ml) and the solid was filtered off. The product was crystallised from isopropanol to afford 2-Acetyl-4-nitroindan-1,3-dione (8.74 g, 79%).

$R_f$ 0.44 (EtOAc/AcOH 100:0.2);

FAB MS $C_{11}H_7NO_5$ (233.17) m/z (%) 256 [M+Na]$^+$ (20), 234 [M+H]$^+$ (100).

$^1$H NMR (CDCl$_3$) δ8.09–7.83 (m, 3H, 3 Ar—H$_{(E,Z)}$), 2.62, 2.60 (2s, 3H, CH$_3$(E,Z)).

It will be apparent to the person skilled in the art that while the invention has been described in some detail for the purposes of clarity and understanding, various modifications and alterations to the embodiments and methods described herein may be made without departing from the scope of the inventive concept disclosed in this invention.

References cited herein are listed on the following pages, and are incorporated by this reference.

REFERENCES

Boullanger, P., Banoub, J. and Descotes, G. Can. J. Chem., 1987 65 1343.
Bovin, N. V., Zurabyan, S. E. and Khorlin, A. Y. Carbohydr. Chem., 1986 5 215.
Buskas, T., Garegg, P. J., Konvadsson, P. and Maloisel, J. L. Tetrahedron Asymmetry, 1994 5 2187.
Bycroft, B. W., Chan, W. C., Chhabra, S. R. and Hone, N. D. J. Chem. Soc. Chem. Commun., 1993 778.
Castro-Palomino, J. C. and Schmidt, R. R. Tetrahedron Lett., 1995 36 5343.
Chan, W. C., Bycroft, B. W., Evans, D. J. and White, P. D. J. Chem. Soc. Chem. Commun., 1995 2209.
Dasgupta, F. and Garegg, P. J. J. Chem. Soc. Chem. Commun., 1989 1640
Fields, G. B. and Noble, R. L. Int. J. Peptide Protein Res., 1990 35 161.
Griffith, D. A. and Danishefsky, S. J. J. Am. Chem. Soc., 1990 112 5811.
Hayakawa, Y., Kato, H., Uchiyama, M., Kajino, H. and Noyori, R. J. Org. Chem., 1986 51 2400.
Imoto, M., Yoshimura, H., Shimamoto, T., Sakahuchi, N., Kusumoto, S. and Shiba, T. Bull. Chem. Soc. Jpn., 1987 60 2205.
Kaifu, R. and Osawa, T. Carbohydr. Res., 1977 58 235.
Lemieux, R. V., Abbas, S. Z. and Chung, B. Y. Can. J. Chem., 1982 60 58.
Lemieux, R. V. and Ratcliffe, R. T. Can. J. Chem., 1979 57 1244.
Mootoo, D. R. and Fraser-Reid. B. Tetrahedron Lett., 1989 30 2363.
Palsen, H. Angew. Chem. Int. Ed. Engl., 1982 21 155.
Paulsen, H. and Stenzel, W., Chem. Ber., 1978 111 2334 & 2348.
Sasaki, T., Minamoto, K. and Itoh, H. J. Org. Chem., 1978 43 2320.
Schmidt, R. R. and Kinzy, W Adv. Carbohydr. Chem. Biochem., 1994 50 21–121.
Shapiro, D., Acher, A. J. and Rachaman, E. S. J. Org. Chem., 1967 32 3767.
Tailler, D., Jacquiaet, J. C., Noirot, A. M. and Bean, J. M. J. Chem. Soc., Perkin. Trans. I, 1992 3163.
Toyokuni, T. and Singhal, A. K. Chem. Soc. Rev., 1995, 231.
Zurabyan, S. E., Antenenko, T. S. and Khorlin, A. Y. Carbohydr. Res., 1994 50 21–121

What is claimed is:

1. A compound comprising a sugar comprising one or more primary amine groups protected with a 2-substituted-1,3-dioxo compound of Formula I or Formula II:

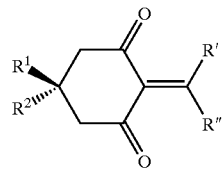

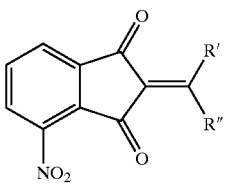

in which
R$^1$ is hydrogen or C$_{1-4}$ alkyl,
R$^2$ is hydrogen or C$_{1-4}$ alkyl,
R' is an amino sugar, a glycosylamine, or an oligosaccharide comprising at least one aminosugar or one glycosylamine unit, in which the sugar is coupled via an amino group,
and R" is alkyl, substituted alkyl, aryl, substituted aryl, cycloalkyl or substituted cycloalkyl.

2. A compound according to claim 1, wherein the protecting group is of Formula I and R$^1$ and R$^2$ are both methyl.

3. A compound according to claim 1, wherein the compound is selected from the group consisting of 2-Deoxy-2-[1-(4,4-dimethyl-2,6-dioxocyclohex-1-ylidene)ethylamino]-D-glucopyranose; 2-Deoxy-2-[1 (4,4-dimethyl-2,6-dioxocyclohex-1-ylidene)ethylamino]-1,3,4,6-tetra-O-acetyl-α-D-glucopyranose; 2-Deoxy-2-[1-(4,4-dimethyl-2,6-dioxocyclohex-1-ylidene)-ethylamino]-3,4,6-tri-O-acetyl-α-D-glucopymanosyl bromide; Methyl 2-Deoxy-2-[1-(4,4-dimethyl-2,6-dioxocyclohex-1-ylidene)ethylamino]-3,4,6-tri-O-acetyl-β-D-glucopyranoside; S-(2-Deoxy-2-[1-(4,4-dimethyl-2,6-dioxocyclohex-1-ylidene)ethylamino]-3,4,6-tri-O-acetyl-β-D-gluco-pyranosyl] isothiouronium bromide; Methyl 2-Deoxy-2-[1-(4,4-dimethyl-2,6-dioxocyclohex-1-ylidene)ethylamino]-1-thio-3,4,6-tri-O-acetyl-β-D-glucopyranoside; Benzyl 2-Deoxy-2-[1-(4,4-dimethyl-2,6-dioxocyclohex-1-ylidene)ethylamino]-α-D-glucopyranoside; 2-Deoxy-2-[1-(4,4-dimethyl-2,6-dioxocyclohex-1-ylidene)ethylamino]-3,4,6-tri-O-acetyl-β-D-glucopyranosyl azide, 2-Deoxy-2-[1-(4,4-dimethyl-2,6-dioxocyclohex-1 -ylidene)ethylamino]-1-thio-3,4,6-tri-O-acetyl-β-D-glucopyranose; Benzyl 4,6-O-Benzylidene-2-deoxy-2-[1-(4,4-dimethyl)-2,6-dioxocyclohex-1-ylidene)-ethylamino]-α-D-glucopyranoside; Benzyl 2-Deoxy-2-[1-(4,4-dimethyl-2,6-dioxocyclohex-1-ylidene)-ethylamino]-3,4,6-tri-O-acetyl-α-D-glucopyranoside; 2-Deoxy-2-[1-(4,4-dimethyl-2,6dioxocyclohex-1-ylidene)ethylamino]-3,4,6-tri-O-acetyl-α-D-glucopyranose; 2-deoxy-2-[1-(4,4-dimethyl-2,6-dioxocyclohex-1-ylidene)ethylamino]-3,4,6-tri-O-acetyl-α,β-D-glucopanosyl trichloroacetimidate; Benzyl 2-Deoxy-2-[1-(4,4-dimethyl-2,6-dioxocyclohex-1-ylidene)ethylamino]-6-O-triphenylmethyl-α-D-glucopyranoside; Benzyl 2-Deoxy-2-[1-(4,4-dimethyl-2,6-dioxocyclohex-1-ylidene)ethylamino]-6-O-t-butyldimethyl-silyl-α-D-glucopyranoside; 2-Deoxy-2-[1-(4,4-dimethyl-2,6-dioxocyclohex-1-ylidene)ethylamino]-3,4,6-tri-O-acetyl-β-D-glucopyranosyl amine; 4-[N-[1-(4,4-dimethyl-2,6-dioxocyclohexylidene)ethyl]-amino]benzyl(1,2,3,4-tetra-O-acetyl-β-D-glucopyranose)uronate; 2-Acetamido-2-deoxy- 3,4,6-tri-O-acetyl-β-D-glucopyranosyl amine, 2-Acetamido-3,4,6-tri-O-acetyl-1,2-dideoxy-1-[1-(4,4-dimethyl-2,6-dioxocyclohex-1-ylidene)ethylamino]-β-D-glucopyranose; Benzyl 2-Deoxy-2-[1-(4,4-dimethyl-2,6-dioxocyclohex-1-ylidene)ethylamino]-4,6-O-isopropylidene-α-D-glucopyranoside; 2-Deoxy-2-[1-(4,4-dimethyl-2,6-dioxocyclohex-1-ylidene)ethylamino]-D-galactopyranose; 2-Deoxy-2-[1-(4-nito-1,3-dioxoindan-2-ylidene)ethylamino]-D-glucopyranose: 2-Deoxy-2-[1-(4-nitro-1,3-dioxoindan-2-ylidene)-ethylamino]-3,4,6-tri-O-acetyl-α-D-glucopyranose; 3'-deoxy-3'-[1-(4,4-dimethyl-2,6-dioxocyclohex-1-ylidene)-ethylamino]-thymidine; 4-O-(2,3,4,6-tetra-O-acetyl-α-galacto-pyranosyl)-2,3,6-tri-O-acetyl-β-D-glucopyranosyl azide; 4-O-(2,3,4,6-tetra-O-acetyl-α-D-galacto-pyranosyl)-2,3,6-tri-O-acetyl-β-D-glucopyranosyl amine; 4-O-(2,3,4,6-tetra-O-acetyl-α-D-galactopyranosyl)-2,3,6-tri-O-acetyl-N-[1-(4,4-dimethyl-2,6dioxocyclohex-1-ylidene)ethyl]-β-D-glucopyranosyl amine; and Methyl 2-Deoxy-2-[1-(4,4-dimethyl-2,6-dioxocyclohex-1-ylidene)ethylamino]-3,4,6-tri-O-acetyl-α-D-glucopyranoside.

4. A linker-saccharide complex, comprising a linker group and a saccharide compound comprising a protecting group of Formula I or Formula II

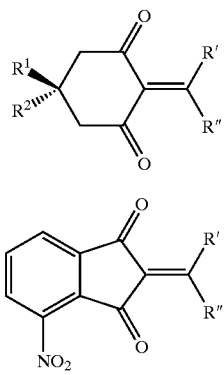

in which
  $R^1$ is hydrogen or $C_{1-4}$ alkyl,
  $R^2$ is hydrogen or $C_{1-4}$ alkyl,
  R' is an amino sugar, a glycosylamine, or an oligosaccharide comprising at least one aminosugar or one glycosylamine unit, in which the sugar is coupled via an amino group,
  and R" is alkyl, substituted alkyl, aryl, substituted aryl, cycloalkyl or substituted cycloalkyl.

5. A method of solution phase synthesis of oligosaccharides, comprising sequentially linking mono- or oligosaccharide groups to a linker-saccharide complex as defined in claim 4.

6. A method according to claim 5, wherein the oligosaccharide comprises an aminoglycoside group.

7. A method according to claim 5, wherein the method is a combinatorial synthetic method.

8. A method of solution phase synthesis of oligosaccharides, comprising sequentially reacting mono- or oligosaccharide groups with a linker-saccharide complex as defined in claim 4, under conditions effective to form glycosidic bonds, thereby sequentially linking said groups to said complex.

9. A linker-saccharide complex for solution phase synthesis of oligosaccharides, comprising a linker group and a saccharide compound comprising a protecting group of Formula I or Formula II

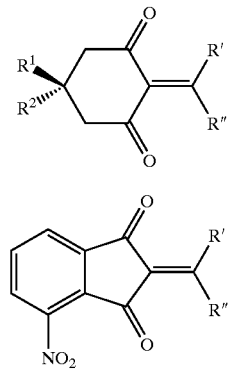

in which
  $R^1$ is hydrogen or $C_{1-4}$ alkyl,
  $R^2$ is hydrogen or $C_{1-4}$ alkyl,
  R' is an amino sugar, a glycosylamine, or an oligosaccharide comprising at least one aminosugar or one glycosylamine unit, in which the sugar is coupled via an amino group, and R" is alkyl, substituted alkyl, aryl, substituted aryl, cycloalkyl or substituted cycloalkyl.

10. A resin-linker-saccharide support for solid phase oligosaccharide synthesis, comprising a linker group, a resin, and a saccharide compound comprising a protecting group of Formula I or Formula II

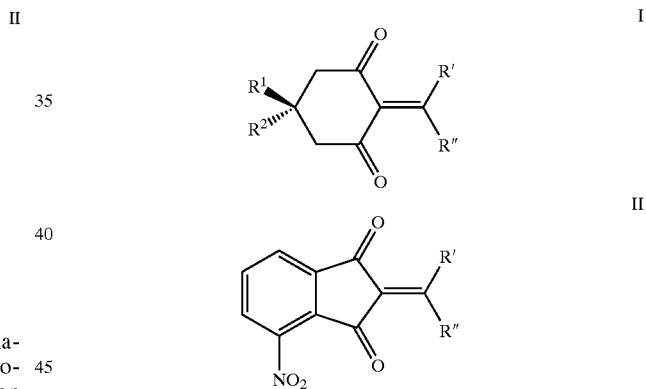

in which
  $R^1$ is hydrogen or $C_{1-4}$ alkyl,
  $R^2$ is hydrogen or $C_{1-4}$ alkyl,
  R' is an amino sugar, a glycosylamine, or an oligosaccharide comprising at least one aminosugar or one glycosylamine unit, in which the sugar is coupled via an amino group,
  and R" is alkyl, substituted alkyl, aryl, substituted aryl, cycloalkyl or substituted cycloalkyl.

11. A method of solid-phase synthesis of oligosaccharides, comprising sequentially linking mono- or oligosaccharide groups to a resin-linker-saccharide support as defined in claim 10.

12. A kit for solid-phase synthesis or combinatorial synthesis of oligosaccharides, comprising a linker-saccharide complex according to claim 6.

13. A kit according to claim 12, further comprising at least a first partially or differentially activated, filly protected saccharide, protecting agent, deprotecting agent, resin or solvent suitable for solid phase or combinatorial synthesis.

14. A kit for solid-phase synthesis or combinatorial synthesis of oligosaccharides, comprising a resin-linker-saccharide support according to claim 10.

15. A kit according to claim 14, further comprising at least a first partially or differentially activated, fully protected saccharide, protecting agent, deprotecting agent, resin or solvent suitable for solid phase or combinatorial synthesis.

16. A method of solid-phase synthesis of oligosaccharides, comprising sequentially reacting mono- or oligosaccharide groups with a resin-linker-saccharide support as defined in claim 10, under conditions effective to form glycosidic bonds, thereby sequentially linking said groups to said support.

17. A resin-linker-saccharide support, comprising a linker group, a resin, and a saccharide compound comprising a protecting group of Formula I or Formula II

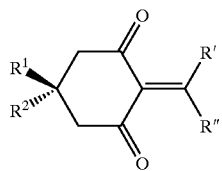

I

-continued

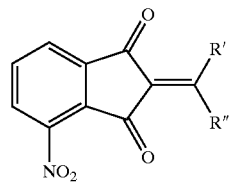

II in which $R^1$ is hydrogen or $C_{1-4}$ alkyl, $R^2$ is hydrogen or $C_{1-4}$ alkyl, R' is an amino sugar, a glycosylamine, or an oligosaccharide comprising at least one aminosugar or one glycosylamine unit, in which the sugar is coupled via an amino group, and R" is alkyl, substituted alkyl, aryl, substituted aryl, cycloalkyl or substituted cycloalkyl.

* * * * *

UNITED STATES PATENT AND TRADEMARK OFFICE
CERTIFICATE OF CORRECTION

PATENT NO.    : 6,462,183 B1
DATED         : October 8, 2002
INVENTOR(S)   : Toth et al.

It is certified that error appears in the above-identified patent and that said Letters Patent is hereby corrected as shown below:

<u>Column 18,</u>
Line 36, delete "glucopymanosyl" and insert -- glucopyranosyl -- therefor.
Line 48, delete "1 -ylidene)" and insert -- 1-ylidene) -- therefor.
Line 50, delete "dimethyl)-" and insert -- dimethyl- -- therefor.
Line 55, delete "6dioxocyclohex" and insert -- 6-dioxocyclohex -- therefor.
Line 58, delete "glycopanosyl" and insert -- glycopyranosyl -- therefor.

Signed and Sealed this

Twenty-eighth Day of January, 2003

JAMES E. ROGAN
*Director of the United States Patent and Trademark Office*